(12) United States Patent
Bertelsen et al.

(10) Patent No.: US 8,846,088 B2
(45) Date of Patent: Sep. 30, 2014

(54) MELT GRANULATION OF A COMPOSITION CONTAINING A CALCIUM-CONTAINING COMPOUND

(75) Inventors: Poul Egon Bertelsen, Roskilde (DK); Peder Mohr Olsen, Kirke Hyllinge (DK); Carsten Martini Nielsen, Soborg (DK); Magnus Wilhelm Tolleshaug, Oslo (NO)

(73) Assignee: Takeda Nycomed AS, Asker (NO)

( * ) Notice: Subject to any disclaimer, the term of this patent is extended or adjusted under 35 U.S.C. 154(b) by 1564 days.

(21) Appl. No.: 11/883,532

(22) PCT Filed: Feb. 2, 2006

(86) PCT No.: PCT/IB2006/000188
§ 371 (c)(1),
(2), (4) Date: Nov. 5, 2008

(87) PCT Pub. No.: WO2006/082499
PCT Pub. Date: Aug. 10, 2006

(65) Prior Publication Data
US 2009/0068268 A1    Mar. 12, 2009

(30) Foreign Application Priority Data

Feb. 3, 2005    (DK) .................................. 2005 00167

(51) Int. Cl.
*A61K 9/36*    (2006.01)
*B29B 9/00*    (2006.01)

(52) U.S. Cl.
USPC .............................................. 424/479; 264/6

(58) Field of Classification Search
USPC ................................................ 424/479; 264/6
See application file for complete search history.

(56) References Cited

U.S. PATENT DOCUMENTS 4,446,135 A    5/1984    Fountaine
(Continued)

FOREIGN PATENT DOCUMENTS

CN    1193026 A    9/1998
DE    20216314 U1    12/2003
(Continued)

OTHER PUBLICATIONS

Bolhuis et al., "DC Calcium lactate, a new filler-binder for direct compaction of tablets", International Journal of Pharmaceuticals, vol. 221, 2001, pp. 77-86.
(Continued)

*Primary Examiner* — Aradhana Sasan
(74) *Attorney, Agent, or Firm* — Edwards Wildman Palmer LLP; Peter F. Corless

(57) ABSTRACT

A novel method for the preparation of a tablet comprising a calcium-containing compound, the method involves a melt granulation process by which a sugar alcohol is melted and embeds the calcium-containing compound so that a sufficient taste masking of the chalkiness is substantially achieved and an unpleasant mouth feel of the calcium-containing compound is substantially avoided, while at the same time obtaining a low tablet volume. The method of the invention is especially suitable for the manufacturing of tablets having a high load of a calcium-containing compound.

31 Claims, 9 Drawing Sheets

Tablet heights (Function of compression force and type of sugar alcohol) (data from example 1).

(56) References Cited

U.S. PATENT DOCUMENTS

| | | | |
|---|---|---|---|
| 4,698,264 | A | 10/1987 | Steinke |
| 4,830,859 | A | 5/1989 | Finnan et al. |
| 5,108,728 | A | 4/1992 | Rau et al. |
| 6,149,941 | A | 11/2000 | Schwarz et al. |
| 2003/0203026 | A1* | 10/2003 | Sherry et al. ............... 424/469 |
| 2003/0211168 | A1 | 11/2003 | Lynenskjold et al. |
| 2004/0071772 | A1 | 4/2004 | Narita et al. |
| 2005/0232989 | A1* | 10/2005 | Piene et al. ............... 424/464 |

FOREIGN PATENT DOCUMENTS

| | | | |
|---|---|---|---|
| EP | 0647591 | A1 | 4/1995 |
| EP | 0872240 | A1 | 10/1998 |
| EP | 0914818 | A1 | 5/1999 |
| EP | 1126017 | A1 | 8/2001 |
| EP | 1369131 | A1 | 12/2003 |
| JP | 01317374 | A | 12/1989 |
| JP | 5306229 | A | 11/1993 |
| JP | 2000342187 | A | 12/2000 |
| JP | 2001-316249 | A | 11/2001 |
| WO | WO-92/10168 | A1 | 6/1992 |
| WO | WO-95/08273 | A1 | 3/1995 |
| WO | WO-96/09036 | | 3/1996 |
| WO | WO-96/09036 | A1 | 3/1996 |
| WO | WO-97/41835 | A1 | 11/1997 |
| WO | WO-99/06051 | A1 | 2/1999 |
| WO | WO-99/59553 | | 11/1999 |
| WO | WO 99/59553 | * | 11/1999 ............... A61K 9/46 |
| WO | WO-00/28973 | | 5/2000 |
| WO | WO-00/28973 | A1 | 5/2000 |
| WO | 00/76650 | A1 | 12/2000 |
| WO | 01/83374 | A2 | 11/2001 |
| WO | WO-03/055500 | A1 | 7/2003 |

OTHER PUBLICATIONS

Bruynseels, et al., "Fluidized-bed process fully established and still developing", Nitrogen No. 183, Jan.-Feb. 1990, pp. 22-26.
CPhI Celebrates ten years of growth in Frankfurt—Manufacturing Chemist, Dec. 31, 1999.
"Excipient Systems", http://www.merck.de/english/services/specialchemie/s_chn/pharma/excipients.htm, Nov. 7, 2000.
Merck Formaxx products—marketing information, Sep. 16, 2004.
Oneda et al., "The effect of formulation variables on the dissolution and physical properties of spray-dried microspheres containing organic salta", Power Technology, vol. 130, 2003, pp. 377-384.
Rumpler et al., "Continuous Agglomeration and Granulation by Fluidization", Food Marketing & Technology, Apr. 1999, pp. 1-3.
De Brabander C. et al. "Matrix mini-tablets based on starch/microcrystalline wax mixtures." Int J Pharm. Apr. 20, 2000;199(2):195-203.
Kidoro M. et al. "Properties of tablets containing granulations of ibuprofen and an acrylic copolymer prepared by thermal processes." Pharm Dev Technol. 2001;6(2):263-75.
Schaefer T. et al. "Effects of powder particle size and binder viscosity on intergranular and intragranular particle size heterogeneity during high shear granulation." Eur J Pharm Sci. Mar. 2004;21(4):525-31.
"2.9.8. Resistance to Crushing of Tablets" European Pharmacopoeia 7.0 p. 267 01/2008:20908.
"2.9.3. Dissolution Test for Solid Dosage Forms" European Pharmacopoeia 7.0 pp. 256-263 01/2010:20903 corrected 6.8.
"2.9.7. Friability of Uncoated Tablets" European Pharmacopoeia 7.0 p. 266 01/2010:20907.
"2.9.1. Disintegration of Tablets and Capsules" European Pharmacopoeia 7.1 pp. 3331-3332 04/2011:20901.
Klobes P et al. "Porosity and Specific Surface Area Measurements for Solid Materials" NIST, (SP 960-17).

* cited by examiner

Sieve analysis from example 1.

Tablet heights (Function of compression force and type of sugar alcohol) (data from example 1).

Tablet crushing strength, function of compression force and type of sugar alcohol (data from example 1).

Tablet heights function of compression force and type of sugar alcohol (data from example 2).

Tablet crushing strength function of compression force and type of sugar alcohol (data from example 2).

Tablet height, effect of kneading (data from example 3).

Tablet crushing strength, effect of kneading (data from example 3).

Sieve analysis from example 2.

MELT GRANULATION OF A COMPOSITION CONTAINING A CALCIUM-CONTAINING COMPOUND

FIELD OF THE INVENTION

The present invention relates to a novel method for the preparation of a tablet comprising a calcium-containing compound, the method involves a melt granulation process by which a sugar alcohol is melted and embeds the calcium-containing compound so that a sufficient taste-masking of the chalkiness is substantially achieved and an unpleasant mouth feel of the calcium-containing compound is substantially avoided, while at the same time obtaining a low tablet volume. The method of the invention is especially suitable for the manufacturing of tablets having a high load of a calcium-containing compound.

In a specific embodiment, a granulate that is suitable for further processing into tablets can be obtained by a melt granulation process carried out in an extruder.

BACKGROUND OF THE INVENTION

Calcium is essential for a number of key functions in the body, both as ionized calcium and a calcium complex. A number of diseases, especially bone-related diseases, are treated/prophylactically treated by intake of a sufficient amount of a calcium-containing compound. Normally, calcium must be orally administered in a relatively high amount, which makes especially dosage forms like e.g. chewable or suckable tablets suitable. However, one of the major problems in this respect is to obtain compositions that have a sufficient customer compliance in order to achieve a correct and efficient treatment. This problem is related to the unpleasant taste and/or mouth feel of calcium-containing compounds, which taste and/or mouth feel is very difficult to mask. Accordingly, the development regarding calcium-containing products for pharmaceutical or nutriceutical use is mainly focused on this taste-masking aspect. To this end, a number of different ways of achieving a suitable taste-masking of a calcium-containing compound have emerged including different manufacturing processes, use of various taste-masking agents and combinations thereof etc.

Another major problem in relation to formulation of calcium-containing solid dosage forms is the size of the dosage form. Normally, a single dose of calcium equals 500 mg (12.5 mmol), which means that, when calcium carbonate is used as calcium source, a single dose contains 1250 mg of calcium carbonate (MW of calcium carbonate is 100). Furthermore, addition of pharmaceutically acceptable excipients is normally required in order to enable tabletting of the calcium-containing compound. This means that the resulting tablet containing a single dose of calcium has a relatively high weight and accordingly, the volume of the tablet is relatively high. It is therefore of utmost importance to seek to minimize the size of the dosage form (e.g. normally in the form of a tablet) as much as possible so that the patient does not find it unpleasant to take the tablet. The size of the tablets is of course of most importance in case of tablets intended for oral administration (to be swallowed). Alternatively, the size of chewing tablets is not that important provided that tablets containing a relevant single dose can be manufactured by means of conventional tabletting equipment. However, in the case dose dispensing is needed the size is critical. Furthermore, chewing tablets should not be too hard to chew, i.e. they should have a crushing strength, which balances the easiness of chewing the tablet and the importance of robustness in order to withstand the normal handling of the tablets. Furthermore, the mouth feel and the taste are of utmost importance in order to ensure patient compliance.

It has been found that the particular method for preparing a particulate material containing the calcium-containing compound influences the taste and mouth-feel of the final product. Thus, it has been found that e.g. a fluid-bed method enables preparation of calcium-containing particulate material that when compressed into tablets have an acceptable taste and mouth-feel in use. In this case, the quality of the calcium-containing compound as well as the method for preparation of a pharmaceutical composition containing the calcium-containing compound are of great importance in order to obtain acceptable taste and mouth feel of a chewable tablet (WO 00/28973). The granulates obtained by this process are manufactured into tablets that have suitable sensory properties, i.e. acceptable mouth feel and taste. However, such tablets must have a suitable small size, a suitable mechanical stability and a suitable mechanical strength to withstand exposure to filling e.g. via a dose-dispensing machine. Furthermore, a fluid-bed process often lead to a very porous granulate which in turn lead to porous tablets, i.e. such tablets may be too large to fit into the cassettes of dose-dispensing machines.

Moreover, the fluid-bed method is not generally applicable to e.g. tablets intended to be sucked or swallowed. The reason is that calcium is dosed in a relatively high amount and in order to include this dosage in a single doses form (tablet), the size of the tablet becomes inconveniently large for a patient to swallow. Accordingly, the fluid-bed process is particular useful in the preparation of chewable tablets, where the size has minor importance.

Calcium-containing tablets suitable for swallowing (i.e. prepared without taking the chalky taste and mouth-feel of the calcium-containing compound into consideration) can be prepared by a process involving e.g. high-shear mixing (WO 96/09036 to Innothera). By using this process a relatively dense granulate is obtained, which in turn leads to tablets of a size that is reduced compared to that obtained when a fluid-bed process is used.

The problem addressed by the present inventors is to provide an alternative method that without preference enables the preparation of a dosage form of a calcium-containing compound in the form of chewable tablets as well as in the form of swallowable tablets. In other words, the known processes are either suitable for use in the preparation of chewable tablets or in the preparation of swallowable tablets. In contrast thereto, a method according to the invention can be used both to prepare chewable tablets and swallowable tablets, respectively.

Such a process has high economical potential, as it will be possible to use the same apparatus in the production of tablets irrespective of whether they are intended for chewing or swallowing. Accordingly, the same production line can easily be shifted from one process to the other and it is not necessary to invest in two separate and different production equipment.

Accordingly, there is a need for developing novel methods that enable preparation of dosage forms like tablets that have a reduced and convenient size for a patient to swallow it and, moreover, also can be used in the preparation of chewable tablets.

Furthermore, due to the difficulty in efficiently masking the chalky taste and the unpleasant mouth feel of calcium, there is a need to develop methods that are suitable for use to obtain an acceptable and good taste.

DESCRIPTION OF THE INVENTION

Figure 1:
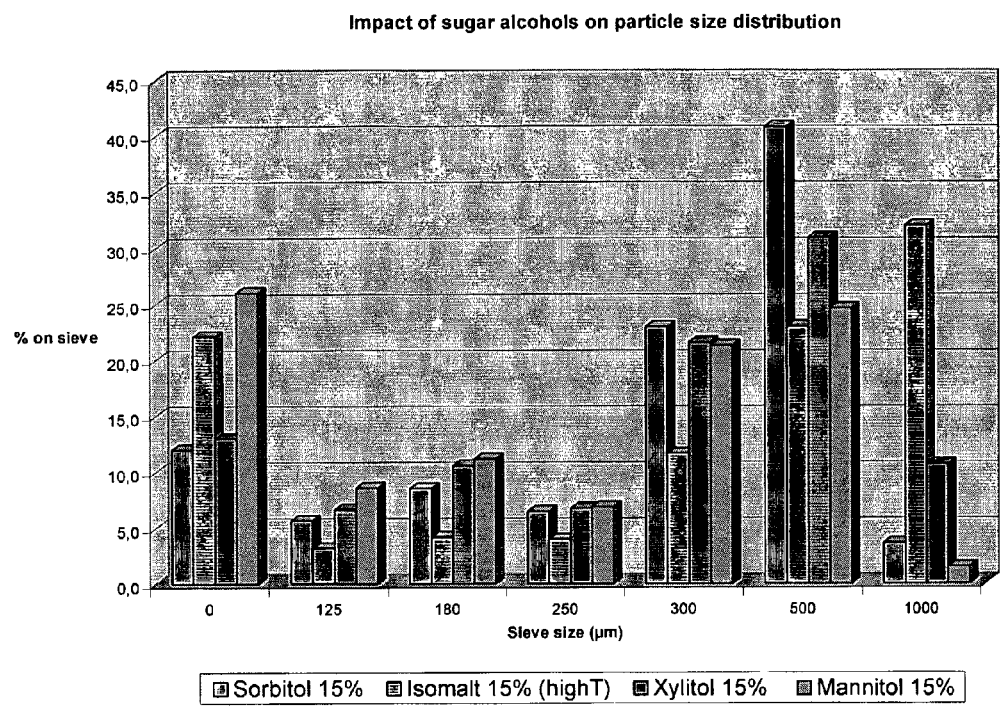
FIG. 1 illustrates the impact of sugar alcohols on particle size distribution based on the sieve analysis from example 1.

Thus, in an aspect of the invention, the present invention provides an efficient and easy way of obtaining a sufficient taste-masking by subjecting a composition containing a calcium-containing compound to a melt granulation process, i.e. a process whereby the particles are agglomerated by means of a melted or at least softened binding agent. In specific embodiments, the binding agent is a sugar alcohol, especially such sugar alcohols that normally are used in taste masking of calcium-containing compounds.

The present invention is based on the finding that melt granulation and/or extrusion of a composition comprising a calcium-containing compound together with a sugar alcohol results in a granulate that has very desirable characteristics with respect to taste and mouth feel. During the extrusion process heating is applied, which melts or softens the sugar alcohol, whereby it at least partly covers the particles of the calcium-containing compound. When compressed into tablets a sugar alcohol matrix is formed. This matrix results in easy wetting of the primary calcium particles when chewing the tablets. The sugar alcohol matrix dissolves in contact with saliva in the mouth. This easy wetting reduces the chalkiness and unpleasant mouth feel.

Furthermore, it has been shown that tablets can be manufactured with lower heights, than can be obtained by known processes such as fluid bed and high shear mixing. A low height facilitates swallowing. A combination of small volume and pleasant mouth feel (less chalkiness) would allow the patient to choose whether to chew or to swallow the tablet.

Accordingly, in one aspect the present invention relates to a method for the preparation of a tablet comprising a calcium-containing compound as an active substance, the method comprising
i) melt granulating a composition comprising the calcium-containing compound with a sugar alcohol,
ii) optionally adding one or more pharmaceutically acceptable excipients, and
iii) compressing the thus obtained granulate into tablets.

Although the present invention is based on the above-mentioned observation resulting from application of an extruder, there is reason to believe that the same way of obtaining a taste masking of a calcium-containing compound could be obtained by other equipment suitable for use for melt granulation. Suitable equipment comprises specially designed high- and low shear mixers for melt granulation. Accordingly, the present invention is not limited to a process for melt granulating by means of extrusion, but all suitable processes are encompassed within the present invention.

Moreover, as mentioned in the introduction the present invention is not limited to the preparation of granulates that are suitable for processing into chewable tablets. As demonstrated in the examples herein, the present method fulfils the need of providing a granulate that—depending on the specific ingredients, the quality thereof and the various process parameters employed—can be designed to be suitable for use in the preparation of chewable, suckable and/or swallowable tablets, respectively or tablets containing all three qualities at the same time.

In a specific aspect, the present invention relates to a method for the preparation of a tablet comprising a calcium-containing compound as an active substance, the method comprising
i) melt granulating a composition comprising the calcium-containing compound by extrusion in a screw extruder
ii) optionally adding one or more pharmaceutically acceptable excipients, and
iii) compressing the thus obtained granulate into tablets.

As mentioned above, in a specific embodiment that lead to a granulate that is especially suitable for further processing into chewable tablets, the granulation is performed by means of melt granulation.

In another specific embodiment melt granulation leads to tablets suitable for swallowing.

In another specific embodiment melt granulation leads to tablets, which are both swallowable and chewable.

Normally, the composition comprises a sugar alcohol that has a melting point of at the most about 160° C.

In the case of an extruder such as e.g. a screw extruder (e.g. a single-, twin- or a triple screw extruder or an extruder designed like a planetary gear (like the Bohle continuous granulater BCG), the melt granulation is effected by heating at least one segment of the screw extruder to a temperature above the melting point of the sugar alcohol. More details appear from the examples herein.

The temperature employed is normally at the most 50° C. above the melting point of the sugar alcohol employed.

In preferred embodiments it is convenient to use a sugar alcohol that has properties like a binder, i.e. to a certain extent it is capable of establishing binding between the individual particles in the composition and further in the binding during compression into coherent tablets. Thus, such sugar alcohols with binding properties facilitate the agglomeration process as well as the tabletting process.

Figure 8:
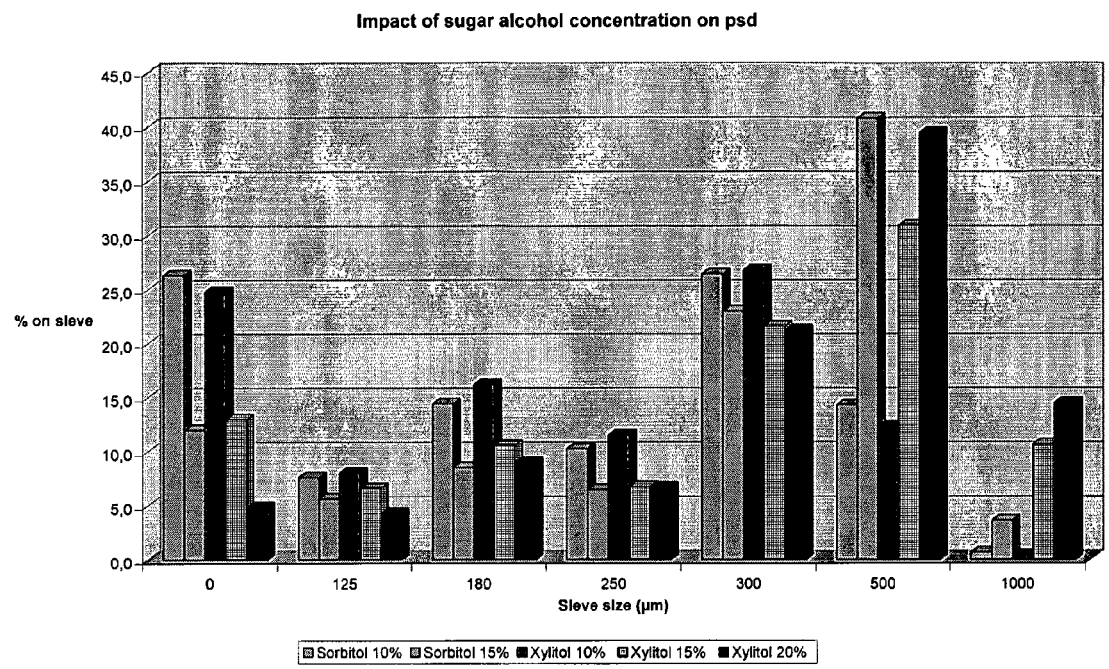
FIG. 8 illustrates the impact of sugar alcohol concentration on psd (particle size distribution) based on the sieve analysis from example 2.
Figure 9:
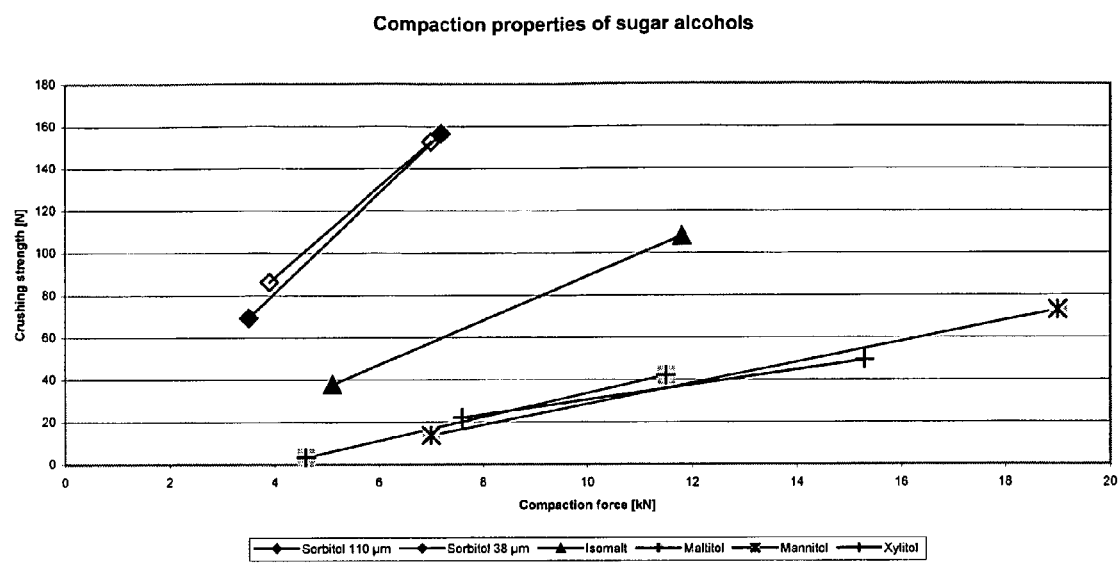
FIG. 9 illustrates the compaction properties of sugar alcohols.

A sugar alcohol suitable for use in methods according to the invention is selected from the group consisting of isomalt, mannitol, sorbitol, xylitol, inositol, erythritol, lactitol, maltitol, and the like, and mixtures thereof. Normally, the concentration of the sugar alcohol in the composition comprising the calcium-containing compound is from about 5% to about 40% w/w such as, e.g., from about 5% to about 35% w/w, from about 10% to about 30% w/w, from about 10% to about 30% w/w, from about 10% to about 25% w/w. In general all the mentioned sugar alcohols may be used as binders. However, the amounts required to obtain suitable binding are dependent on the binding properties of the sugar alcohol in question. FIG. 8 herein gives a graphical representation of crushing strength as a function of compaction force for various sugar alcohols and from this graph it is seen that sugar alcohols with lower slopes are required in higher amounts than sugar alcohols with steeper slopes.

In specific embodiments, the sugar alcohol is the sole binder used in the composition of the invention, but in other embodiments it may be used in combination with other binders. Typically other melt binders may be employed such as, e.g., polyethylene glycols (PEG), PVP, HPMC, waxes, fats and lipids.

The concentration of the binder in the composition comprising the calcium-containing compound may vary over a great range depending on the particular binder employed, but in general it is between from about 0.1% to about 40% w/w such as, e.g. from about 0.2 to about 35% w/w, from about 0.3 to about 30% w/w or from about 0.4 to about 25% w/w or from about 0.4 to about 24.2% w/w.

Irrespective of whether a sugar alcohol has been employed as a binder or not, one or more sugar alcohols (e.g. such as those mentioned hereinbefore) are included in specific embodiments. The sugar alcohols have sweetening and taste masking properties in themselves, which make them especially suitable for use in the present context. The concentration of the sugar alcohol in the composition comprising the calcium-containing compound (or, alternatively, in the granulate obtained) is from about 5% to about 40% w/w such as, e.g., from about 5% to about 35% w/w, from about 10% to about 30% w/w, from about 10% to about 30% w/w, from about 10% to about 25% w/w.

As it appears from the examples herein, it is preferred that a screw extruder does not employ a kneading zone. The use of kneading leads to stronger, but higher tablets. However, the screw elements necessary for the kneading cause severe friction during the extrusion. This can only be solved by the lubricating effect of the melted sugar alcohol, which implies a restriction in how low an amount of sugar alcohol that can be applied.

In another aspect, the invention provides a granulate obtained by the granulation step of the method described herein, wherein the individual granules at least partly are covered with a sugar alcohol and wherein the porosity of the granulate obtained is lower than that obtained employing a fluid-bed and/or a high-shear mixer process, all other conditions unchanged.

The tablets comprising the calcium-containing compound may consist of the calcium-containing compound as such or it may also comprise one or more pharmaceutically acceptable excipients such as described herein. If it is desired to prepare a combination product, i.e. a product containing more than one therapeutically, prophylactically and/or diagnostically active substance, the composition may also comprise one or more of such substances. To this end it should be mentioned that combination products of calcium and a nutrient like e.g. vitamin D already are on the market and have proved to be efficient in therapy. However, due to vitamin D sensibility towards humidity and oxidation, vitamin D is normally added to the granulate before e.g. compression into tablets, i.e. vitamin D is not subjected to the granulate step of the process of the invention.

Calcium-Containing Compound

The calcium-containing compound contained in a granulated composition made according to the invention is a physiologically tolerable calcium-containing compound that is therapeutically and/or prophylactically active.

Calcium is essential for a number of key functions in the body, both as ionized calcium and a calcium complex (Campell A K. Clin Sci 1987; 72:1-10). Cell behaviour and growth are regulated by calcium. In association with troponin, calcium controls muscle contraction and relaxation (Ebashi S. Proc R Soc Lond 1980; 207:259-86).

Calcium selected channels are a universal feature of the cell membrane and the electrical activity of nerve tissue and the discharge of neurosecretory granules are a function of the balance between intracellular and extra cellular calcium levels (Burgoyne R D. Biochim Biophys Acta 1984; 779:201-16). The secretion of hormones and the activity of key enzymes and proteins are dependent on calcium. Finally calcium as a calcium phosphate complex confers rigidity and strength on the skeleton (Boskey A L. Springer, 1988: 171-26). Because bone contains over 99% of the total body calcium, skeletal calcium also serves as the major long-term calcium reservoir.

Calcium salts such as, e.g., calcium carbonate or calcium phosphate is used as a source of calcium especially for patients suffering from or at risk of osteoporosis. Moreover, calcium carbonate is used as an acid-neutralizing agent in antacid tablets.

As mentioned above, calcium has a number of important functions within the mammalian body in particular in humans. Furthermore, in many animal models, chronic low calcium intake produces osteopenia. The osteopenia affects cancellous bone more than cortical bone and may not be completely reversible with calcium supplementation. If the animal is growing reduced calcium intake leads to stunting. In the premature human neonate the higher the calcium intake, the greater the increase in skeletal calcium accretion which, if high enough, can equal gestational calcium retention. During growth chronic calcium deficiency causes rickets. Calcium supplements in both pre- and postpubertal healthy children leads to increased bone mass. In adolescents the higher the calcium intake, the greater the calcium retention, with the highest retention occurring just after menarche. Taken together, these data suggest that in children and adolescents considered to be taking an adequate intake of calcium, peak bone mass can be optimized by supplementing the diet with calcium. The mechanisms involved in optimizing deposition of calcium in the skeleton during growth are unknown. They are probably innate properties of the mineralization process that ensures optimal calcification of the osteoid if calcium supplies are high. The factors responsible for stunting of growth in states of calcium deficiency are also unknown but clearly involve growth factors regulating skeletal size.

In adults calcium supplementation reduces the rate of age-related bone loss (Dawson-Hughes B. Am J Clin Nut 1991; 54:S274-80). Calcium supplements are important for individuals who cannot or will nor achieve optimal calcium intakes from food. Furthermore, calcium supplement is important in the prevention and treatment of osteoporosis etc.

Furthermore, calcium may have anticancer actions within the colon. Several preliminary studies have shown high calcium diets or intake of calcium supplementation is associated with reduced colon rectal cancer. There is increasing evidence that calcium in combination with acetylsalicylic acid (ASA) and other non-steroidal anti-inflammatory drugs (NSAIDS) reduce the risk the risk of colorectal cancer.

Recent research studies suggest that calcium might relieve premenstrual syndrome (PMS). Some researchers believe that disruptions in calcium regulation are an underlying factor in the development of PMS symptoms. In one study, half the women of a 466 person group of pre-menopausal women from across the U.S. were tracked for three menstrual cycles and were given 1200 mg of calcium supplements daily throughout the cycle. The final results showed that 48% of the women who took placebo had PMS related symptoms. Only 30% of those receiving calcium tablets did.

Calcium salts like e.g. calcium carbonate is used in tablets and due to the high dose of calcium required, such tablets are often in the form of chewable tablets. It is a challenge to formulate e.g. chewable tablets containing a calcium salt, which tablets have a pleasant taste and an acceptable mouth feel without the characteristic dominating taste or feeling of chalk.

A calcium-containing compound for use according to the invention may be e.g. bisglycino calcium, calcium acetate, calcium carbonate, calcium chloride, calcium citrate, calcium citrate malate, calcium cornate, calcium fluoride, calcium glubionate, calcium gluconate, calcium glycerophosphate, calcium hydrogen phosphate, calcium hydroxyapatite, calcium lactate, calcium lactobionate, calcium lactogluconate, calcium phosphate, calcium pidolate, calcium stearate and tricalcium phosphate. Other calcium sources may be water-soluble calcium salts, or complexes like e.g. calcium alginate, calcium-EDTA and the like or organic compounds containing calcium like e.g. calcium organophosphates. Use of bone meal, dolomite and other unrefined calcium sources is discouraged because these sources may contain lead and other toxic contaminants. However, such sources may be relevant if they are purified to a desired degree.

The calcium-containing compound may be used alone or in combination with other calcium-containing compounds.

Of specific interest is bisglycino calcium, calcium acetate, calcium carbonate, calcium chloride, calcium citrate, calcium citrate malate, calcium cornate, calcium fluoride, calcium glubionate, calcium gluconate, calcium glycerophosphate, calcium hydrogen phosphate, calcium hydroxyapatite, calcium lactate, calcium lactobionate, calcium lactogluconate, calcium phosphate, calcium pidolate, calcium stearate and tricalcium phosphate. Mixtures of different calcium-containing compounds may also be used. As appears from the examples herein, calcium carbonate and calcium phosphates are especially suitable for use as a calcium-containing compound and calcium carbonate, tricalcium phosphate ($Ca_5(PO_4)OH$) and 1-tricalcium phosphate ($Ca_3(PO_4)$) have a high content of calcium, whereas dicalcium phosphate ($CaHPO_4$) has a lower content of calcium but is available in high density qualities.

Of particular interest is calcium carbonate and calcium phosphate.

Normally, a tablet made according to the invention contains an amount of the calcium-containing compound corresponding to from about 100 to about 1000 mg Ca such as, e.g., from about 150 to about 800 mg, from about 200 to about 700 mg, from about 200 to about 600 mg or from about 200 to about 500 mg Ca.

Calcium Carbonate

Calcium carbonate can be in three different crystal structures: calcite, aragonite and vaterite. Mineralogically, these are specific mineral phases, which relate to the distinct arrangement of the calcium, carbon and oxygen atoms in the crystal structure. These distinct phases influence the shape and symmetry of the crystal forms. For example, calcite is available in four different shapes: scalenohedral, prismatic, spherical and rhombohedral, and aragonit crystals can be obtained as e.g. discrete or clustered needle-like shapes. Other shapes are also available such as, e.g., cubic shapes (Scoralite 1A+B from Scora).

As shown in the examples herein, a particular suitable quality of calcium carbonate is calcium carbonate having a mean particle size of 60 μm or less such as, e.g., 50 μm or less or 40 μm or less.

Furthermore, an interesting quality of calcium carbonate has a bulk density below 2 g/mL.

Calcium carbonate 2064 Merck (available from Merck, Darmstadt, Germany) that has a mean particle size of 10-30 μm, an apparent bulk density of 0.4 to 0.7 g/mL, and a specific surface area of 0.3 m²/g;

Calcium carbonate 2069 Merck (available from Merck, Darmstadt, Germany) that has a mean particle size of approx. 3.9 μm, and an apparent bulk density of 0.4 to 0.7 g/mL;

Scoralite 1A (available from Scora Watrigant SA, France) has a mean particle size of 5 to 20 μm, an apparent bulk density of 0.7 to 1.0 g/mL, and a specific surface area of 0.6 m²/g;

Scoralite 1B (available from Scora Watrigant SA, France) has a mean particle size of 10-25 μm, an apparent bulk density of 0.9 to 1.2 g/mL, and a specific surface area of 0.4 to 0.6 m²/g;

Scoralite 1A+B (available from Scora Watrigant SA, France) have a mean particle size of 7-25 μm, an apparent bulk density of 0.7 to 1.2 g/mL, and a specific surface area of 0.35 to 0.8 m²/g;

Pharmacarb LL (available from Chr. Hansen, Mahawah New Jersie) L has a mean particle size of 12-16 μm, an apparent bulk density of 1.0 to 1.5 g/mL, and a specific surface area of 0.7 m²/g;

Sturcal H (available from Specialty Minerals, Bethlehem, Pa.) has a mean particle size of approx. 4 μm, an apparent bulk density of 0.48 to 0.61 g/mL;

Sturcal F (available from Specialty Minerals, Bethlehem, Pa.) has a mean particle size of approx. 2.5 μm, an apparent bulk density of 0.32 to 0.43 g/mL;

Sturcal M (available from Specialty Minerals, Bethlehem, Pa.) has a mean particle size of 7 μm, an apparent bulk density of 0.7 to 1.0 g/mL, and a specific surface area of 1.5 m²/g;

Sturcal L (available from Specialty Minerals, Bethlehem, Pa.) has a mean particle size of approx. 7 μm, an apparent bulk density of 0.78 to 0.96 g/mL, Sturcal L consists of scalenohedral shaped crystals;

Socal P2PHV (available from Solvay, Brussels, Belgium) has a mean particle size of 1.5 μm, an apparent bulk density of 0.28 g/mL, and a specific surface area of 7.0 m²/g Socal P2PHV consists of scalenohedral shaped crystals;

Mikhart 10, SPL, 15, 40 and 65 (available from Provencale, Provencale, France);

Mikhart 10 has a mean particle size of 10 μm,

Mikhart SPL has a mean particle size of 20 μm,

Mikhart 15 has a mean particle size of 17 μm,

Mikhart 40 has a mean particle size of 30 μm, an apparent bulk density of 1.1 to 1.5 g/mL;

Mikhart 65 has a mean particle size of 60 μm, an apparent bulk density of 1.25 to 1.7 g/mL;

Hubercal Elite 500 (available from J.M. Huber Corp., USA) has a mean particle size of 5.8 μm and a specific surface area of 1.8 m²/g;

Hubercal Elite 500 (available from J.M. Huber Corp., USA) has a mean particle size of 8.2 μm and a specific surface area of 1.3 m²/g.

Omyapure 35, (available from Omya S.A.S, Paris, France) has a mean particle size of 5-30 μm, and a specific surface area of 2.9 m²/g;

Calci Pure 250 Heavy, Calci Pure 250 Extra Heavy and Calci Pure GCC HD 212 with a mean particle size of 10-30 μm, an apparent bulk density of 0.9-1.2 g/ml, and a specific surface area of 0.7 m²/g (available from Particle Dynamic Inc., St. Louis Mont.).

Calcium Phosphate

DI-CAFOS A ($CaHPO_4$) (available from Chemische Fabrik Buddenheim KG, Buddenheim, Germany) that has a mean particle size of approximately 70 μm and a bulk density of approximately 1.3 g/ml and a polycrystalic and porous nature;

DI-CAFOS PA (CaHPO$_4$) (available from Chemische Fabrik Buddenheim KG, Buddenheim, Germany) that has a mean particle size <7 μm and a bulk density of approximately 0.9 g/ml;

TRI-CAFOS P (Ca$_5$(PO$_4$)$_3$OH (available from Chemische Fabrik Buddenheim KG, Buddenheim, Germany) that has a mean particle size <6 μm and a bulk density of approximately 0.25 g/ml and a polycrystalic and porous nature;

TRI-CAFOS S (Ca$_5$(PO$_4$)$_3$OH (available from Chemische Fabrik Buddenheim KG, Buddenheim, Germany) that has a mean particle size of approximately 70 μm and a bulk density of approximately 0.5 g/ml;

CAFOS DB (Ca$_3$(PO$_4$)$_2$ (available from Chemische Fabrik Buddenheim KG, Buddenheim, Germany) that has a mean particle size <5 μm and a bulk density of approximately 0.6 g/ml;

Other qualities may also be suitable for use according to the invention.

The content of the calcium-containing compound in a tablet made according to the present invention is in a range from about 60% to about 100% w/w such as, e.g., from about 65% to about 98% w/w, from about 70% to about 95% w/w, from about 75% to about 95% w/w or at least about 60% w/w, at least about 65% w/w, at least about 70% w/w or at least about 75% w/w.

Normally, the dose of calcium for therapeutic or prophylactic purposes is from about 350 mg (e.g. newborn) to about 1200 mg (lactating women) daily. The amount of the calcium-containing compound in the tablets can be adjusted to that the tablets are suitable for administration 1-4 times daily, preferably once or twice daily.

As mentioned above, the granulate obtained by the granulation step of the method according to the invention may be used as such, but it is also very suitable for further manufacturing into solid dosage forms like e.g. tablets, capsules or sachets.

In the examples herein guidance is given of which parameters that are important to take into account and how to select a suitable set-up in order to prepare chewable tablets or swallowable tablets, respectively. Based on this guidance a person skilled in the art will know how to adjust the composition and the various process parameters in order to obtain a desired calcium-containing product.

In one aspect of the invention, the granulate obtained by the granulation step of present method is intended to be manufactured into tablets. Often it is necessary to add one or more pharmaceutically acceptable excipients (e.g. lubricants) in order to avoid adherence and/or increase flowability of the granulate obtained. Accordingly, the method may also comprise a step of mixing the granulate obtained with one or more pharmaceutically acceptable excipients.

In the event that it is desired to include other active substances than the calcium-containing compound, the method may also comprise a step of adding one or more therapeutically, prophylactically and/or diagnostically active substance to the granulate obtained.

Such substances include one or more nutrients such as, e.g., one or more vitamins or minerals. In a specific embodiment, the further active substance is a D-vitamin such as, e.g., D$_3$ vitamin, D$_2$ vitamin or derivatives thereof.

D Vitamin or Other Active Substances

A granulate or tablet made according to the invention may comprise a further therapeutically and/or prophylactically active substance, or it may contain one or more nutrients such as, e.g. one or more vitamins or minerals. Of specific interest are e.g. vitamin B, vitamin C, vitamin D and/or vitamin K and minerals like e.g. zinc, magnesium, selenium etc.

Of particular interest are one or more D-vitamin compounds such as, e.g., Vitamin D$_2$ (ergocalciferol) and Vitamin D$_3$ (cholecalciferol) including dry vitamin D$_3$, 100 CWS available from Roche and dry vitamin D$_3$ 100 GFP available from BASF.

In addition to its action on calcium and skeletal homeostasis, vitamin D is involved in the regulation of several major systems in the body. The actions of vitamin D are medicated at the genome by a complex formed by 1,25-(OH)$_2$ vitamin D mainly produced in the kidney, with the vitamin D receptor (VDR). The latter is widely distributed in many cell types. The 1,25-(OH)$_2$ vitamin DNDR complex has important regulatory roles in cell differentiation and in the immune system. Some of these actions are probably dependant on the ability of certain tissues other than the kidney to produce 1,25-(OH)$_2$ vitamin D locally and act as a paracrine (Adams J S et al. Endocrinology 1996; 137:4514-7).

In humans, deficiency of vitamin D results in rickets in children and osteomalacia in adults. The basic abnormality is a delay in the rate of mineralization off osteoid as it is laid down by the osteoblast (Peacock M. London Livingstone, 1993: 83-118). It is not clear whether this delay is due to a failure of a 1,25-(OH)$_2$ vitamin D-dependant mechanism in the osteoblast or to reduced supplies of calcium and phosphate secondary to malabsorption or a combination of both. Accompanying the mineralization delay, there is reduced supply of calcium and phosphate, severe secondary hyperparathyroidism with hypocalcemia and hypophosphatemia and increased bone turnover.

Vitamin D insufficiency, the preclinical phase of vitamin D deficiency, also causes a reduced calcium supply and secondary hyperparathyroidism, albeit of a milder degree than found with deficiency. If this state remains chronic, osteopenia results. The biochemical process underlying this state of calcium insufficiency is probably inappropriate level of 1,25-(OH)$_2$ vitamin D due to a reduction in its substrate 25-OHD (Francis R M et al. Eur J Clin Invest 1983; 13:391-6). The state of vitamin D insufficiency is most commonly found in the elderly. With age there is a decrease in serum 25-OH vitamin D due to decreased sunlight exposure and possible to decreased skin synthesis. Furthermore, in the elderly the condition is exacerbated by a decrease in calcium intake and a paradoxical decrease in calcium absorption. The reduction in renal function with age giving rise to reduced renal 1,25-(OH)$_2$ vitamin D production may be a contributing factor. There are a number of studies of the effects of vitamin D supplementation on bone loss in the elderly. Some are without calcium supplementation and others are with calcium supplementation. It appears from the studies that although vitamin D supplementation is necessary to reverse deficiency and insufficiency, it is even more important as far as the skeleton is concerned to provide calcium supplementation since the major skeletal defect is calcium deficiency. In literature based on clinical trials, recent findings suggest trends of need for higher doses of vitamin D for the elderly patients (Compston J E. BMJ 1998; 317:1466-67). An open quasi-randomised study of annual injections of 150.000-300.000 IU of vitamin D (corresponding to approx. 400-800 IU/day) showed a significant reduction in overall fracture rate but not in the rate of hip fracture in treated patients (Heikinheimo R J et al. Calcif Tissue Int 1992; 51:105-110).

As it appears from above, a combination of calcium and vitamin D is of interest. The recommended Daily Allowance (RDA) of calcium and vitamin D$_3$ are as follows (European Commission. Report on osteoporosis in the European Community. Action for prevention. Office for official Publications of the European Communities, Luxembourg 1998):

| Group | Age (years) | Calcium (mg)* | Vitamin D$_3$ (µg) |
|---|---|---|---|
| Newborn | 0-0.5 | 400 | 10-25 |
|  | 0.5-1.0 | 360-400 | 10-25 |
| Children | 1.0-3.0 | 400-600 | 10 |
|  | 4.0-7.0 | 450-600 | 0-10 |
|  | 8.0-10 | 550-700 | 0-10 |
| Men | 11-17 | 900-1000 | 0-10 |
|  | 18-24 | 900-1000 | 0-15 |
|  | 25-65 | 700-800 | 0-10 |
|  | 65+ | 700-800 | 10 |
| Women | 11-17 | 900-1000 | 0-15 |
|  | 18-24 | 900-1000 | 0-10 |
|  | 25-50 | 700-800 | 0-10 |
|  | 51-65 | 800 | 0-10 |
|  | 65+ | 700-800 | 10 |
| Pregnant |  | 700-900 | 10 |
| Lactating |  | 1200 | 10 |

*RDA of calcium varies from country to country and is being re-evaluated in many countries.

Vitamin D is very sensitive towards humidity and is subject to degradation. Therefore, vitamin D is often administered in a protective matrix. Accordingly, when tablets are prepared containing a vitamin D it is of utmost importance that the compression forces applied during the tabletting step do not decrease the protective effect of the matrix and thereby impair the stability of vitamin D. To this end, the combination of the various ingredients in a granulate or tablet made according to the invention has proved to be very suitable in those cases where vitamin D also is incorporated into the composition as it is possible to employ a relatively low compression force during tabletting and still achieve a tablet with suitable mechanical strength (crushing strength, friability etc.).

Accordingly, the compression step is performed at a compression force that is adjusted with respect to the diameter and the desired height of the tablet so that the compression force applied is at the most 50 kN, at the most about 40 kN, at the most about 30 kN or at the most about 25 kN such as at the most about 20 kN.

In a specific embodiment, the invention provides a tablet comprising
i) a calcium-containing compound as an active substance,
ii) a vitamin D, and
iii) optionally one or more pharmaceutically acceptable excipients.

More specifically, the tablet may comprise
i) at least 200 mg of the calcium-containing compound (normal range 200-1500 mg),
ii) at least 5 µg of vitamin D (normal range 5-100 µg–1 µg=40 IU), and
iii) optionally one or more pharmaceutically acceptable excipients.

In a specific embodiment, the invention provides a tablet comprising
i) from about 50% to about 90% w/w of the calcium-containing compound,
ii) from about 0.00029% o about 0.0122% w/w of a vitamin D, and
iii) optionally one or more pharmaceutically acceptable excipients
with the proviso that the total amount of ingredients corresponds to about 100% w/w.

In particular, the tablet may comprise
i) from about 50% to about 90% w/w of the calcium-containing compound,
ii) from about 5 to about 40% w/w of a sweetening agent,
iii) from about 0.12% to about 4.9% w/w of a vitamin D including a protective matrix,
iv) optionally one or more pharmaceutically acceptable excipients
with the proviso that the total amount of ingredients corresponds to about 100% w/w.

Preparation of a Tablet According to the Invention

The method according to the invention may also comprise compression of a granulate obtained as described herein optionally in admixture with one or more pharmaceutically acceptable excipients.

In general, tablets can be prepared by any suitable process known to a person skilled in the art provided that the granulate is obtained by melt granulation. A person skilled in the art will know how to employ the different techniques optionally with guidance from Remington's The Science and Practice of Pharmacy (2003).

Normally, the amount of the calcium-containing compound in a tablet corresponds to from about 100 to about 1000 mg Ca such as, e.g., from about 150 to about 800 mg, from about 200 to about 700 mg, from about 200 to about 600 mg or from about 200 to about 500 mg Ca.

In a specific embodiment of the invention, the crushing strength of the tablets are adjusted by balancing at least one of:
i) the concentration of sorbitol contained in the composition comprising the calcium-containing compound,
ii) the concentration of xylitol contained in the composition comprising the calcium-containing compound,
iii) the concentration of sorbitol added extragranularly to the granulate
iv) the concentration of xylitol added extragranularly to the granulate.

Pharmaceutically Acceptable Excipients

In the present context, the term "pharmaceutically acceptable excipient" is intended to denote any material, which is inert in the sense that it substantially does not have any therapeutic and/or prophylactic effect per se. A pharmaceutically acceptable excipient may be added to the active drug substance with the purpose of making it possible to obtain a pharmaceutical composition, which has acceptable technical properties.

The calcium-containing compound is normally admixed with one or more pharmaceutically acceptable excipients before compression into tablets. Such excipients include those normally used in formulation of solid dosage forms such as, e.g. fillers, binders, disintegrants, lubricants, flavouring agents, colouring agents, including sweeteners, pH adjusting agents, buffering agents, stabilizing agents, etc. In the following are given examples of excipients suitable for use in a tablet prepared according to the present invention.

| Excipient | Concentration [% of formulation] |
|---|---|
| Sweetening agents | 5-40, if present |
| Artificial sweeteners | 0.05-0.3, if present |
| Flavours | 0.1-3, if present |
| Disintegrating agents | 0.5-5, if present |
| Glidant and lubricants | 0.1-5, if present |
| Fillers/diluents/binders | 0.1-40, if present |
| Film forming agents | 0.1-5, if present |
| Film additives | 0.05-5, if present |

As it appears from the examples herein, the use of xylitol seems to result in tablets having a poor crushing strength. An improvement of the crushing strength can be obtained by adding a granulate containing sorbitol (especially a blend of granulates, each containing 15% of sugar alcohol). Accordingly, in specific embodiments the composition comprising the calcium-containing compound further comprise
i) sorbitol and/or
ii) xylitol.

A method according to the invention may also comprises step of adding xylitol and/or sorbitol to the granulate obtained (i.e. after the melt granulation process).

Sweetening Agents

Examples of suitable sweeteners include dextrose, erythritol, fructose, glycerin, glucose, inositol, isomalt, lactitol, lactose, maltitol, maltose, mannitol, sorbitol, sucrose, tagatose, trehalose, xylitol, etc. Sorbitols e.g. Neosorb P100T, Sorbidex P166B0 and Sorbogem Fines Crystalline Sorbitol available from Roquette Freres, Cerestar and SPI Polyols Inc. respectively. Maltisorb P90 (maltitol) available from Roquette Freres, Xylitol CM50, Fructofin CM (fructose) and Lactitol CM50 available from Danisco Sweeteners, Isomalt ST-PF, Gaio Tagatose and Manitol available from Palatinit, Arla Foods and Roquette, Freres respectively. Sorbitol has a sweetening effect (compared to sucrose) of 0.55; maltitol that has a sweetening effect of <1; xylitol that has a sweetening effect of 1, isomalt that has a sweetening effect of <0.5, etc. The sweetening effect may be of value in connection with choosing the individual sweetening agents. Thus, if a decreased tablet weight and volume are desired, it is suitable to choose a sweetening agent having a high sweetening effect.

Artificial Sweeteners

Acesulfam potassium, alitame, aspartame, cyclamic acid, cyclamate salt (e.g. calcium cyclamate, sodium cyclamate), neohesperidine dihydrochalcone, neohesperidine hydrochloride, saccharin, saccharin salt (e.g. ammonium saccharin, calcium saccharin, potassium saccharin, sodium saccharin), sucralose, taumatin and mixtures thereof.

Flavours

Aprocot, Lemon, Lemon/Lime, Lime, Orange, Mandarine, such as Aprocot 501.110 AP0551, Lemon 501.051 TP0551, Lemon 501.162 AP0551, Lemon/Lime 501.053 TP0551, Lime 501.054 TP0551, Orange 501.071 AP0551, Orange TP0551, Orange 501.434 P0551, Mandarine 501.AP0551, Lemon Durarome 501.282 TDI1091 available from Firmenich, Kerpen, Germany or Juicy Lemon Flavouring T3602 available from TasteTech, Bristol, England or Lemon Lime Flavour Permseal 11029-31, Lemon Flavour Permaseal 12028-31, Lemon Flavour Ultradseal 96918-71 Available from Givaudan Schweiz AG, Kemptthal, Schweiz or Lemon Flavour Powder 605786, Lemon Flavour Powder 605897 available from Frey+Lau Gmbh, Henstedt-Ulzburg, Germany Disintegrating Agents Alginic acid—alginates, carboxymethylcellulose calcium, carboxymethylcellulose sodium, crospovidone, hydroxypropylcellulose, hydroxypropylmethylcellulose (HPMC), cellulose derivatives such as low-substituted hydroxypropylcellulose (e.g LH 11, LH 20, LH 21, LH 22, LH 30, LH 31, LH 32 available from Shin-Etsu Chemical Co.) and microcrystalline cellulose, polacrilin potassium or sodium, polyacrylic acid, polycarbofil, polyethylene glycol, polyvinylacetate, polyvinylpyrrolidone (e.g. Polyvidon® CL, Polyvidon® CL-M, Kollidon® CL, Polyplasdone® XL, Polyplasdone® XL-10); sodium carboxymethyl starch (e.g. Primogel® and Explotab®), sodium croscarmellose (i.e. cross-linked carboxymethylcellulose sodium salt; e.g. Ac-Di-Sol®), sodium starch glycolate, starches (e.g potato starch, maize starch, rice starch), pre-gelatinised starch.

Those skilled in the art will appreciate that it is desirable for compressible tablets to disintegrate within 30 minutes, more desirable within 15 min, most desirable within 5 min; therefore, the disintegrant used preferably results in the disintegration of the tablet within 30 minutes, more preferable within 15 min, most preferable within 5 min. However, for tablets solely meant for chewing, a somewhat longer disintegration time is allowed.

Effervescent agent (e.g. mixture of sodium hydrogen carbonate (carbonates, alkaline, alkaline earth metals) and citric acid (tartaric acid, fumaric acid etc.)).

Glidants and Lubricants

Glidants and lubricants may be incorporated such as stearic acid, metallic stearates, talc, waxes and glycerides with high melting temperatures, hydrogenated vegetable oils, colloidal silica, sodium stearyl fumarate, polyethyleneglycols and alkyl sulphates.

Suitable lubricants include talc, magnesium stearate, calcium stearate, stearic acid, hydrogenated vegetable oils and the like. Preferably, magnesium stearate is used.

Fillers/Diluents/Binders

Dextrins, maltodextrins (e.g. Lodex® 5 and Lodex® 10), dextrose, fructose, glucose, inositol, erythritol, isomalt, lactitol, lactose (e.g., spray-dried lactose, α-lactose, β-lactose, Tabletose®, various grades of Pharmatose®, Microtose or Fast-Floc®), maltitol, maltose, mannitol, sorbitol, sucrose, tagatose, trehalose, xylitol, low-substituted hydroxypropylcellulose (e.g LH 11, LH 20, LH 21, LH 22, LH 30, LH 31, LH 32 available from Shin-Etsu Chemical Co.), microcrystalline cellulose (e.g., various grades of Avicel®, such as Avicel® PH101, Avicel® PH102 or Avicel® PH105, Elcema® P100, Emcocel®, Vivacel®, Ming Tai® and Solka-Floc®), starches or modified starches (e.g potato starch, maize starch, rice starch, pre-gelatinised starch), polyvinylpyrrolidone, polyvinylpyrrolidonelvinyl acetate copolymer, agar (e.g. sodium alginate), calcium hydrogen phosphate, calcium phosphate (e.g. basic calcium phosphate, calcium hydrogen phosphate), calcium sulphate, carboxyalkylcellulose, dextrates, dibasic calcium phosphate, gelatine, gummi arabicum, hydroxypropyl cellulose, hydroxypropylmethylcellulose, magnesium carbonate, magnesium chloride, methylcellulose, polyethylene glycol, polyethylene oxide, polysaccharides e.g. dextran, soy polysaccharide, sodium carbonate, sodium chloride, sodium phosphate.

Surfactants/Enhancers

Surfactants may be employed such as

Non-ionic (e.g., polysorbate 20, polysorbate 21, polysorbate 40, polysorbate 60, polysorbate 61, polysorbate 65, polysorbate 80, polysorbate 81, polysorbate 85, polysorbate 120, sorbitan monoisostearate, sorbitan monolaurate, sorbitan monopalmitate, sorbitan monostearate, sorbitan monooleate, sorbitan sesquioleate, sorbitan trioleate, glyceryl monooleate and polyvinylalkohol), anionic (e.g., docusate sodium and sodium lauryl sulphate)

cationic (e.g., benzalkonium chloride, benzethonium chloride and cetrimide).

Fatty acids, fatty alcohols and fatty esters, for example: ethyl oleate, sodium oleate, lauric acid, methyl laurate, oleic acid, sodium caprate Dioctyl calcium sulfosuccinate, dioctyl potassium sulfosuccinate, dodecyltrimethylammonium bromide, hexadecyltrimethylammonium bromide, trimethyltetradecylammonium bromide, polyoxyethylene ethers (polyoxyethylene-9-lauryl ether), sodium dodecyl sulphate, sodium dioctyl sulfosuccinate, sodium laurate, sodium 5-methoxysalicylate, sodium salicylate;

bile salts, for example:

sodium deoxycholate, deoxycholic acid, sodium cholate, cholic acid, sodium glycocholate, sodium glycodeoxycholate, sodium taurocholate, sodium taurodeoxycholate;

cytoadhesives, for example:
lectins (e.g. *Lycopersicon Esculentum* Agglutinin, Wheat Germ Agglutinin, *Urtica Dioica* Agglutinin).
N-acylated amino acids (especially N-[8-(2-hydroxy-4-methoxy)benzoyl]amino caprylic acid (4-MOAC), 4-[4-(2-hydroxybenzoyl)amino]butyric acid, sodium N-[8-(2-hydroxybenzoyl)amino]-caprylate);
phospholipids, for example:
hexadecylphosphocholine, dimyristoylphosphatidylglycerol, lysophosphatidylglycerol, phosphatidylinositol, 1,2-di (2,4-octadecadienoyl)-sn-glycerol-3-phosphorylcholine and phosphatidylcholines (e.g. didecanoyl-L-phosphatidylcholine, dilauroylphosphatidylcholine, dipalmitoylphosphatidylcholine, distearoylphosphatidylcholine), lysophosphatidylcholine is of particular interest;
cyclodextrins, for example:
β-cyclodextrin, dimethyl-β-cyclodextrin, γ-cyclodextrin, hydroxypropyl β-cyclodextrin, methyl cyclodextrin; especially dimethyl-β-cyclodextrin is of particular interest;
fusidic acid derivatives, for example:
sodium taurodihydrofusidate, sodium glycodihydrofusidate, sodium phosphate-dihydrofusidate; especially sodium taurodihydrofusidate is of particular interest;
others:
sodium salts of e.g. glycyrrhizic acid, capric acid, alkanes (e.g. azacycloalkanes), amines and amides (e.g. N-methyl-pyrrolidone, Azone), amino acids and modified amino acids compounds (e.g. acetyl-L-cysteine), polyols (e.g. propyleneglycol, hydrogels), sulfoxides (e.g. dimethylsulfoxide), terpenes (e.g. carvone), ammonium glycyrrizinate, hyluronic acid, isopropyl myristate, n-lauryl-beta-D-maltopyranoside, saponins, DL-octanonylcarnitine chloride, palmitoyl-DL-carnitine chloride, DL-stearoylcarnitine chloride, acylcarnitines, ethylenediaminedihydro-chloride, phosphate-dihydrofusidate, sodium CAP); especially n-lauryl-beta-D-maltopyranoside is of particular interest, alpha 1000 peptide, peptide MW<1000 comprising at least 6 mol % of aspartatic- and glutamic Acid, decomposed royal jelly, prebiotica, butyrate, butyric acid, vitamin $D_2$, vitamin $D_3$, hydroxy-vitamin $D_3$, 1.25-dihydroxy-vitamin $D_3$, spirulina, proteoglycan, soyahydrolysate, lysin, lactic acid, di-fructose-anhydrid, vylitol Ca-(lactate), hydrolyzate of casein in particular a caseinoglycomacropeptide, negative ionization of $CaCO_3$, acetylsalicylic acid, vitamin K, creatin.

Film Forming Agents

The dosage form may be provided with a coating. Hydrofilic film formers such as hydroxypropylmethylcellulose (HPMC) (e.g. HPMC E5, HPMC E15), hydroxyethylcellulose, hydroxypropylcellulose, polydextrose and maltodextrin, Sepifilm™ and Sepifilm™ LP available from Seppic S.A., Pharmacoat® available from Shin-Etsu Chemical Co, Opadry® available form Colorcon and Kolicoat® available from BASF.

Film Additives

Acetylated monoglyceride, acetyltributyl, acetyltributyl citrate, acetyltriethyl citrate, benzyl benzoate, calcium stearate, castor oil, cetanol, chlorebutanol, colloidal silica dioxide, dibutyl phthalate, dibutyl sebacate, diethyl oxalate, diethyl malate, diethyl maleate, diethyl malonate, diethyl fumarate, diethyl phthalate, diethyl sebacate, diethyl succinate, dimethylphthalate, dioctyl phthalate, glycerin, glyceroltributyrate, glyceroltriacetate, glyceryl behanate, glyceryl monostearate, hydrogenated vegetable oil, lecithin, leucine, magnesium silicate, magnesium stearate, polyethylene glycol, propylene, glycol, polysorbate, silicone, stearic acid, talc, titanium dioxide, triacetin, tributyl citrate, triethyl citrate, zinc stearate, wax.

Other Aspects of the Invention

The present invention also relates to granulates and solid dosage form obtained by the method of the invention. More specifically, the present invention provides a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and wherein the granulate has been obtained by the method according to the present invention;

a composition containing a vitamin D in admixture with a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and wherein the calcium-containing granulate has been obtained by the method according to the present invention;

a composition containing a vitamin $D_2$ and/or $D_3$ in admixture with a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and wherein the calcium-containing granulate has been obtained by the method according to the present invention;

a granulate comprising a vitamin D and a calcium-containing compound, notably calcium carbonate or calcium phosphate or a mixture thereof, in a concentration of at least 60% w/w such as, e.g., at least 70% w/w, at least 75% w/w, or at least 80% w/w and wherein the calcium-containing granulate has been obtained by the method according to the present invention;

a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 5% w/w, and wherein the granulate has been obtained by the method according to the present invention;

a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 10% w/w, and wherein the granulate has been obtained by the method according to the present invention;

a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 15% w/w, and wherein the granulate has been obtained by the method according to the present invention;

a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 20% w/w, and wherein the granulate has been obtained by the method according to the present invention;

a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of about 25% w/w, and wherein the granulate has been obtained by the method according to the present invention;

a composition containing a vitamin D in admixture with a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 5% w/w, and wherein the calcium-containing granulate has been obtained by the method according to the present invention;

a composition containing a vitamin D in admixture with a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 10% w/w, and wherein the calcium-containing granulate has been obtained by the method according to the present invention;

a composition containing a vitamin D in admixture with a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 15% w/w, and wherein the calcium-containing granulate has been obtained by the method according to the present invention;

a composition containing a vitamin D in admixture with a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 20% w/w, and wherein the calcium-containing granulate has been obtained by the method according to the present invention;

a composition containing a vitamin D in admixture with a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of about 25% w/w, and wherein the calcium-containing granulate has been obtained by the method according to the present invention;

a composition containing a vitamin $D_2$ and/or $D_3$ in admixture with a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 5% w/w, and wherein the calcium-containing granulate has been obtained by the method according to the present invention;

a composition containing a vitamin $D_2$ and/or $D_3$ in admixture with a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 10% w/w, and wherein the calcium-containing granulate has been obtained by the method according to the present invention;

a composition containing a vitamin $D_2$ and/or $D_3$ in admixture with a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 15% w/w, and wherein the calcium-containing granulate has been obtained by the method according to the present invention;

a composition containing a vitamin $D_2$ and/or $D_3$ in admixture with a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 20% w/w, and wherein the calcium-containing granulate has been obtained by the method according to the present invention;

a composition containing a vitamin $D_2$ and/or $D_3$ in admixture with a granulate comprising a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of about 25% w/w, and wherein the calcium-containing granulate has been obtained by the method according to the present invention;

a granulate comprising a vitamin D and a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 5% w/w, and wherein the calcium-containing granulate has been obtained by the method according to the present invention;

a granulate comprising a vitamin D and a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 10% w/w, and wherein the calcium-containing granulate has been obtained by the method according to the present invention;

a granulate comprising a vitamin D and a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 15% w/w, and wherein the calcium-containing granulate has been obtained by the method according to the present invention;

a granulate comprising a vitamin D and a calcium-containing compound, notably calcium carbonate or calcium phosphate or a mixture thereof, in a concentration of at least 60% w/w such as, e.g., at least 70% w/w, at least 75% w/w, or at least 80% w/w and a sugar alcohol in a concentration of at least 20% w/w, and wherein the calcium-containing granulate has been obtained by the method according to the present invention;

a granulate comprising a vitamin D and a calcium-containing compound, notably calcium carbonate or calcium phosphate or a mixture thereof, in a concentration of at least 60% w/w such as, e.g., at least 70% w/w, at least 75% w/w, or at least 80% W/W and a sugar alcohol in a concentration of about 25% w/w, and wherein the calcium-containing granulate has been obtained by the method according to the present invention.

Furthermore, the invention provides tablets, notably chewing tablets, comprising one or more of the above-mentioned granulates or compositions.

The invention is further illustrated in the following non-limiting examples.

Materials and methods

Methods

Crushing strength: According to Ph. Eur. 2.9.8

Tablet height: Using a Micro 2000 (made by Moore & Wright (Sheffield) Ltd)

In the examples below, the following materials have been employed:

| | | |
|---|---|---|
| Scoralite 1 B mainstream | Scora Watrigant S.A., France | Calcium carbonate |
| Xylitol CM 50 | Danisco Sweeteners, Kotka, Finland | Xylitol |

-continued

| | | |
|---|---|---|
| Kollidon 30 | BASF AG, Ludwigshafen, Germany | Polyvinylpyrrolidone 30 (PVP 30) |
| Magnesium stearate | Peter Greven Netherland C.V | Magnesium stearate |
| Neosorb P100T | Roquette Freres, Estrem, France | Sorbitol |
| Isomalt ST-PF | Palatinit | Isomalt |
| Manitol 60 | Roquette Freres, Estrem, France | Manitol |

The following non-limiting examples are designed to illustrate the invention. In order to provide guidance for a person skilled in the art of how to select process parameters as well as how to select suitable ingredients as well as suitable qualities thereof, the present examples are mainly focused on a relatively fixed composition of ingredients. However, a person skilled in the art will know how to adjust the process parameters as well as ingredients and qualities thereof based on the content herein. Accordingly, the present invention is not limited to the specific compositions mentioned in the examples below.

Example 1

Melt Granulation, Impact of Different Sugar Alcohols on Granulate Particle Size, Tablet Crushing Strength and Tablet Height Calcium carbonate and sugar alcohol were mixed in a Bohle tumbling mixer at 25 rpm for 15 minutes, batch size approximately 2 kg. This mixture was melt granulated by the use of a Leistritz twin screw extruder MIC 27GL/28D, 8.4 kW. The used process parameters and compositions are shown in table 1.

TABLE 1

| Sugar alcohol | | Powder flow | Screw speed | Temperature profile, segments; ° C. | | | | | | |
|---|---|---|---|---|---|---|---|---|---|---|
| Type | Conc % | g/min | rpm | start | 2 | 3 | 4 | 5 | 6 | end |
| Sorbitol | 15 | 100 | 100 | 60 | 120 | 120 | 120 | 120 | 150 | 150 |
| Isomalt | 15 | 100 | 100 | 87 | 170 | 170 | 170 | 170 | 190 | 190 |
| Xylitol | 15 | 100 | 100 | 60 | 120 | 120 | 120 | 120 | 150 | 150 |
| Mannitol | 15 | 100 | 100 | 87 | 170 | 170 | 170 | 170 | 190 | 190 |

The granulates were cooled at room temperature and characterized by sieve analysis. The results of the sieve analysis are shown in FIG. 1, the following sieves were used 1000 μm, 500 μm, 300 μm, 250 μm, 180 μm, and 125 μm.

A mixture comprising a 1:1 blend of the sorbitol and xylitol granulates was manufactured by use of a Erweka tumbling mixer at 27 rpm for 5 minutes, batch size between 0.5 kg and 1 kg.

Figure 2:
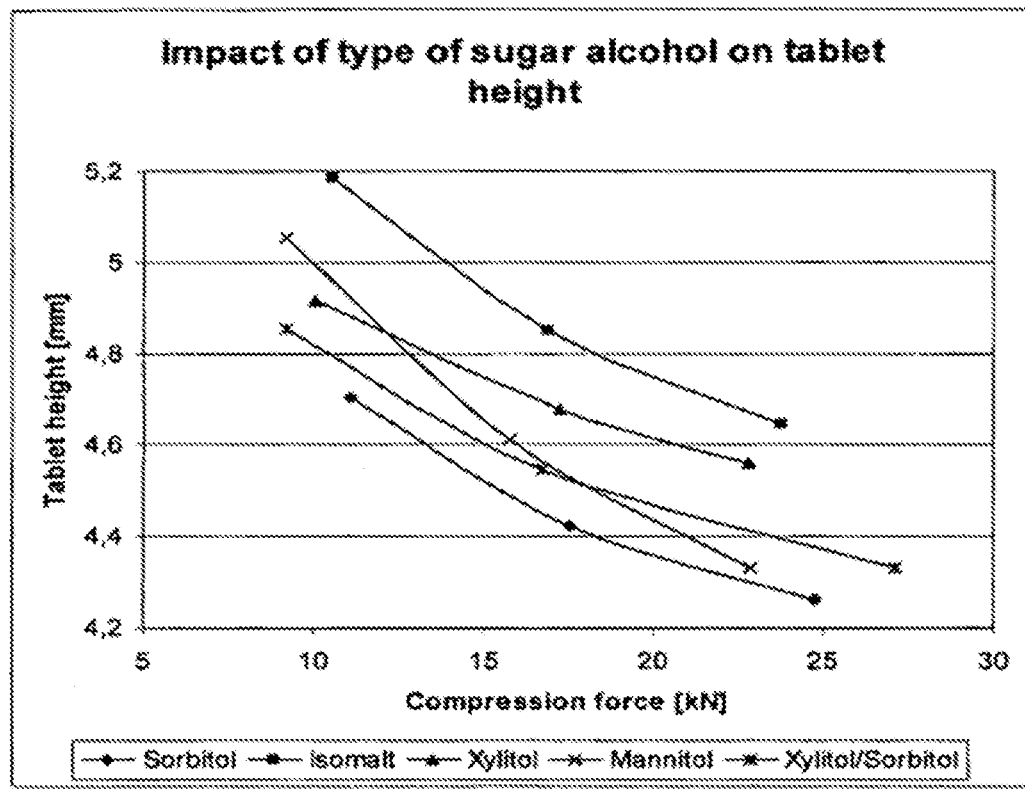
FIG. 2 illustrates the impact of type of sugar alcohol on tablet height based on data from example 1.
Figure 3:
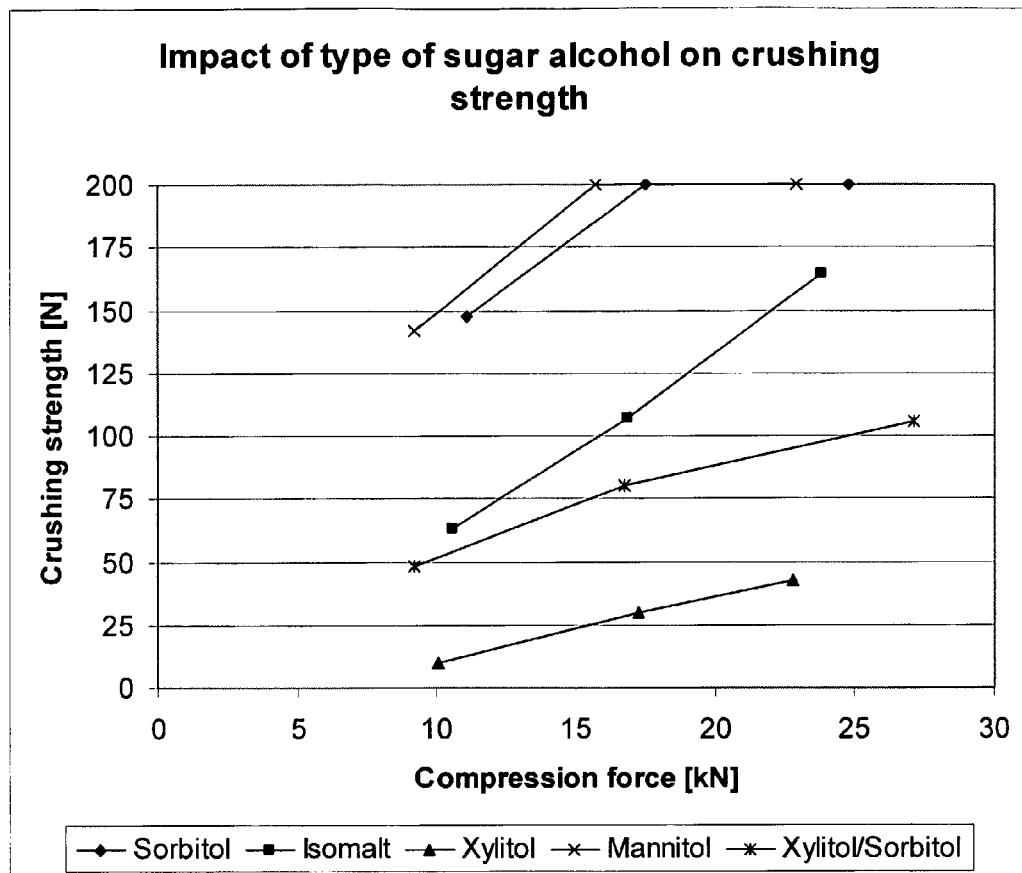
FIG. 3 illustrates the impact of type of sugar alcohol on crushing strength based on data from example 1.

The granulates were mixed with 0.35% w/w magnesium stearate by use of an Erweka tumbling mixer at 27 rpm for 5 minutes, batch size between 0.5 kg and 2 kg. Tablets were manufactured by use of a Korsch PH106 instrumented rotary press and 14 mm round punches.
Target of tablet mass: 1200 mg
Target of compression force: 10 kN, 17 kN and 24 kN.
Die table rpm: 20
The tablets were characterized by crushing strength and tablet height measured two days after manufacture.
The results are shown in FIGS. 2 and 3 from which it is seen that tablets comprising mannitol and sorbitol have a higher crushing strength compared to tablets comprising xylitol. Moreover, using a mixture of sorbitol and xylitol results in tablets with crushing strengths between that of sorbitol and xylitol, whereas the use of xylitol results in tablets with poor crushing strength.

The use of isomalt causes increased tablet height and a crushing strength between that of sorbitol and the sorbitol/xylitol mixture.

The results show that sorbitol and mannitol result in very hard tablets (above 200 N) even at a relatively low compression force (approximately 17 kN) whereas the use of xylitol results in tablets with too low a crushing strength (below 50 N at a compression force of approximately 23 kN). However the crushing strength can be manipulated by the mixing of sorbitol and xylitol, this is also the case for mannitol and xylitol mixtures.

The hard tablets will due to the low tablet height increase the swallowability of the tablets, which will be an advantage for tablets containing high amounts of active ingredients.

However, higher tablets are due to the relatively lower hardness (and higher porosity) desirable when manufacturing chewable tablets. Therefore the mixing of sorbitol and xylitol can be of interest.)

In the following table 2 is shown the relationship between the sugar alcohol employed and the tablet height and crushing strength at various compression forces employed. A score corresponding to 1-5 is given and in respect of tablet height a score of 1 corresponds to the lowest tablet and 5 is the highest, whereas in respect of crushing strength a score of 1 corresponds to the highest crushing strength and 5 is the lowest.

TABLE 2

| | Tablet height | | | Crushing strength | | |
|---|---|---|---|---|---|---|
| Sugar alcohol | 10 kN | 17 kN | 24 kN | 10 kN | 17 kN | 24 kN |
| xylitol | 3 | 4 | 4 | 5 | 5 | 5 |
| sorbitol | 1 | 1 | 1 | 2 | 2 | 1 |
| xylitol/sorbitol | 2 | 2 | 3 | 4 | 4 | 4 |
| mannitol | 4 | 3 | 2 | 1 | 1 | 1 |
| isomalt | 5 | 5 | 5 | 3 | 3 | 3 |

The table shown above gives guidance as to how to select a sugar alcohol that is suitable for use depending on the desired type of dosage form. Accordingly, in the case of a tablet suitable for oral administration and intended to be swallowed it is important to obtain tablets that are as small as possible and at the same time they must have a sufficient robustness to withstand normal handling of the tablets. Furthermore, due to the mouth feel and taste of the tablets, they should not disintegrate already in the mouth, i.e. they should not have a too low crushing strength. From the table it is seen that sugar alcohols like e.g. sorbitol and mannitol are suitable for this application using the twin screw apparatus for the preparation of the granulate. In contrast thereto, sugar alcohols like e.g. isomalt, and a combination of xylitol and sorbitol seem to be of choice in the case of chewing tablets provided that the taste and mouth feel are acceptable.

As apparent from FIG. 1 the particle size distribution (psd) for isomalt comprising granulate contains more coarse particles (above 1000 μm) than the other three sugar alcohols.

Based on a preliminary sensoric test and without being bound by theory the calcium carbonate particles seem to be partly embedded in the sugar alcohol granulate. This means that melt granulation process and the following tabletting process results in a sugar alcohol matrix containing the calcium carbonate.

Example 2

Melt Granulation, Impact of Different Concentrations of Sugar Alcohols on Granulate Particle Size, Tablet Crushing Strength and Tablet Height Granulates and tablets were manufactured and characterized according to Example 1. The used process parameters and compositions are shown in Table 3.

TABLE 3

| Sugar alcohol | | Powder flow | Screw speed | Temperature profile, segments; ° C. | | | | | | |
|---|---|---|---|---|---|---|---|---|---|---|
| type | Conc % | g/min | rpm | start | 2 | 3 | 4 | 5 | 6 | end |
| sorbitol | 10 | 100 | 100 | 60 | 120 | 120 | 120 | 120 | 150 | 150 |
| sorbitol | 15 | 100 | 100 | 60 | 120 | 120 | 120 | 120 | 150 | 150 |
| xylitol | 10 | 100 | 100 | 60 | 120 | 120 | 120 | 120 | 150 | 150 |
| xylitol | 15 | 100 | 100 | 60 | 120 | 120 | 120 | 120 | 150 | 150 |
| xylitol | 20 | 100 | 100 | 60 | 120 | 120 | 120 | 120 | 150 | 150 |

Mixtures comprising a 1:1 blend of sorbitol (10% w/w) and xylitol (10% w/w) and a 1:1 blend of sorbitol (15% w/w) and xylitol (15% w/w) granulates were manufactured by use of a Erweka tumbling mixer at 27 rpm for 5 minutes, batch size between 0.5 kg and 1 kg.

Figure 4:
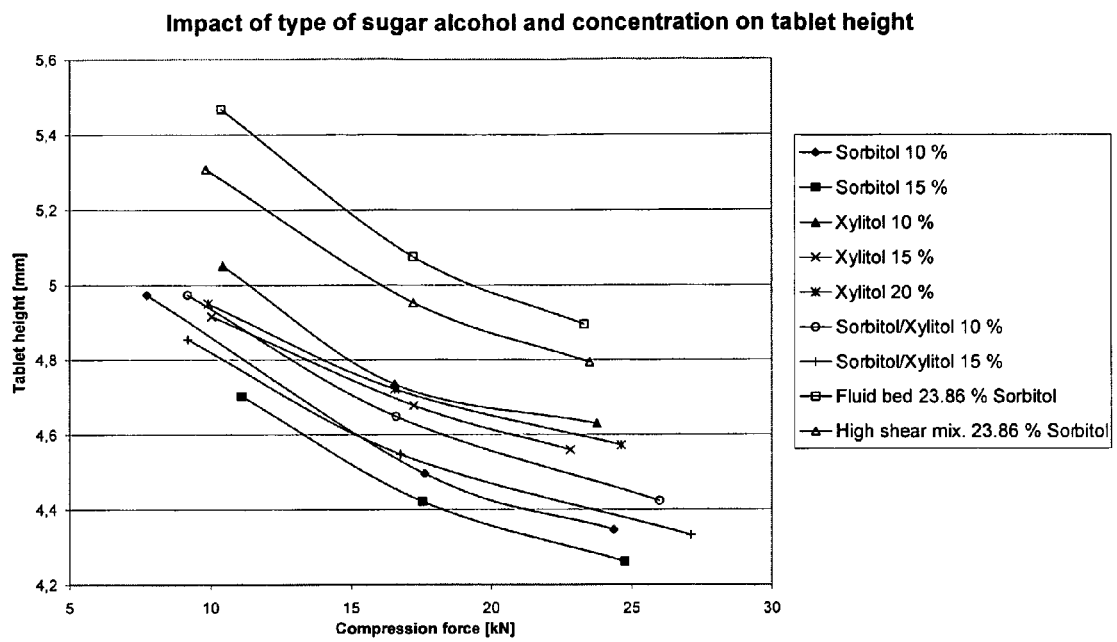
FIG. 4 illustrates the impact of type of sugar alcohol and concentration on tablet height based on data from example 2.
Figure 5:
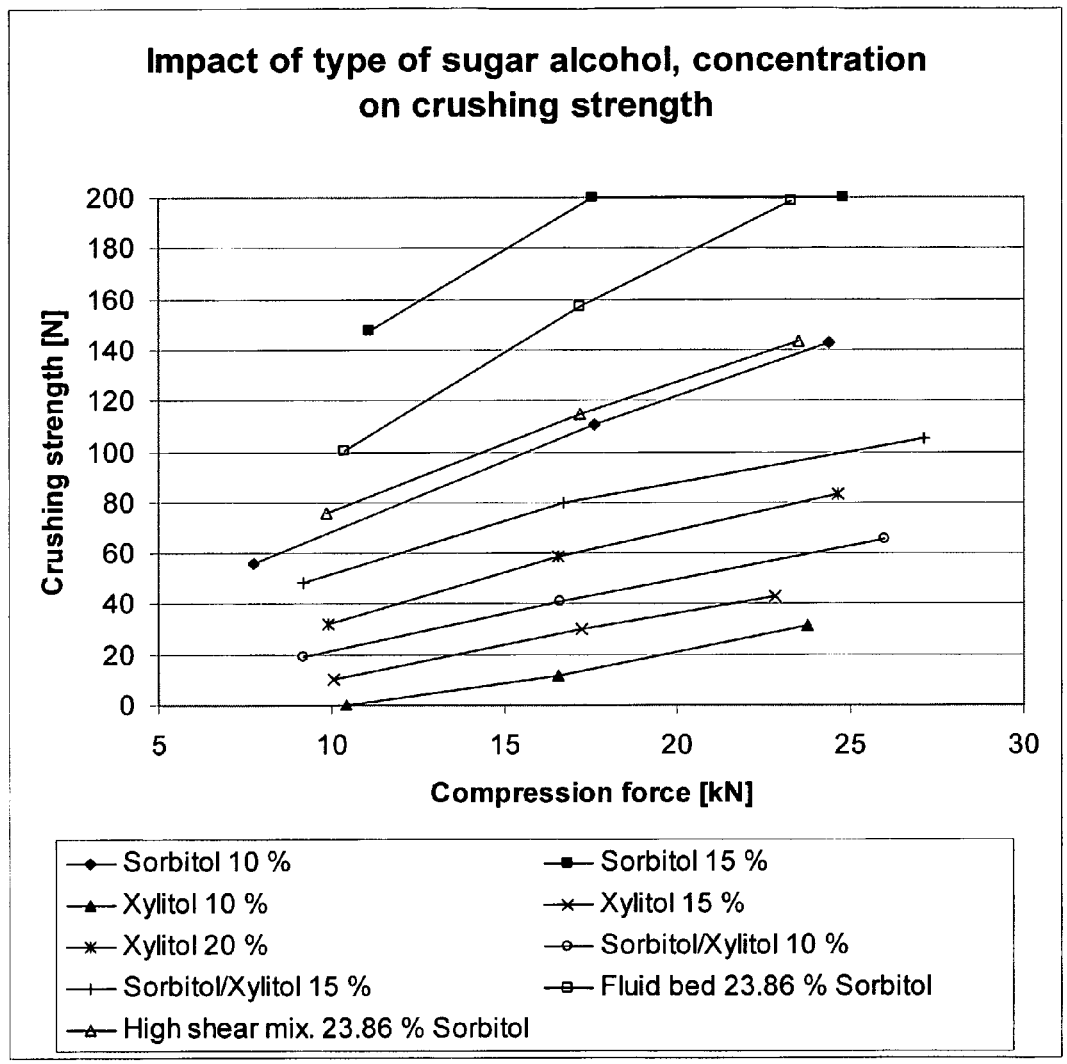
FIG. 5 illustrates the impact of type of sugar alcohol and concentration on crushing strength based on data from example 2.

The results are shown in FIGS. 4 and 5 and in Table 4 below.

The analysis of the results obtained with xylitol, sorbitol and the sorbitoli/xylitol mixture and the reference batches (fluid bed and high shear mixer) shows that:

All concentrations of xylitol results in tablets with poor tablet crushing strengths even though increasing concentrations lead to increasing tablet crushing strength Increasing concentration of sorbitol increases tablet crushing strength Compression forces above 17 kN results in high tablet crushing strengths 1:1 blends of sorbitol 15% and xylitol 15% lead to intermediate tablet crushing strengths. This effect is less pronounced for 1:1 blends of sorbitol 10% and xylitol 10%

The use of sugar alcohols as binder in melt granulation results in tablets with a significantly lower tablet height and increased tablet crushing strength than tablets based on wet granulation in fluid bed and high shear mixer granulates. Furthermore, much lower concentration of sugar alcohols is required by the melt granulation process than by the fluid bed or high-shear mixer process Increased concentration of sugar alcohol decreases tablet height. However the impact is less pronounced for xylitol Increased concentration of sugar alcohol increases granulate particle size (FIG. 8)

In conclusion, the process according to the present invention makes it possible to prepare a granulate that is suitable for use in the preparation of tablets, notably chewable tablets which also are swallowable. First of all, it is possible to obtain a reduced size of the tablet compared to wet granulation processes like e.g. a fluid bed process (see e.g. WO 02/23973) and a high-shear mixer process (FR 2 724 844 to Innothera), which makes the tablet more convenient for the patient to chew or allows the patient to swallow the tablet. The reduction in size is obtained without increasing the hardness of the tablet. On the contrary, it seems that the hardness (expressed as the crushing strength) is slightly decreased with the exception of tablets based on sorbitol 15%, i.e. the tablets may be much easier to chew as well.

TABLE 4

| | Tablet height | | | Crushing strength | | |
|---|---|---|---|---|---|---|
| Sugar alcohol | 10 kN | 17 kN | 24 kN | 10 kN | 17 kN | 24 kN |
| Sorbitol 10% | 3 | 2 | 2 | 4 | 4 | 4 |
| Sorbitol 15% | 1 | 1 | 1 | 1 | 1 | 2 |
| Xylitol 10% | 7 | 7 | 7 | 9 | 9 | 9 |
| Xylitol 15% | 4 | 5 | 5 | 8 | 8 | 8 |
| Xylitol 20% | 6 | 6 | 6 | 6 | 6 | 6 |
| Sorbitol/xylitol 10% | 5 | 4 | 4 | 7 | 7 | 7 |
| Sorbitol/xylitol 15% | 2 | 3 | 3 | 5 | 5 | 5 |
| Fluid bed Sorbitol 23.86% | 9 | 9 | 9 | 2 | 2 | 1 |
| High-shear Sorbitol 23.86% | 8 | 8 | 8 | 3 | 3 | 3 |

Example 3

Melt Granulation, Impact of Kneading on Granulate Particle Size, Tablet Crushing Strength and Tablet Height Granulates and tablets were manufactured using the Leistritz twin screw extruder MIC 27GL/28D with and without a kneading zone inserted. The tablets were characterised according to Example 1. The used process parameters and compositions are shown in Table 5.

TABLE 5

| Sugar alcohol | | Powder flow | Die plate | Screw speed | Temperature profile, segments; ° C. | | | | | | |
|---|---|---|---|---|---|---|---|---|---|---|---|
| Type | Conc % | g/min | Kneading | (sold) | Rpm | start | 2 | 3 | 4 | 5 | 6 | end |
| Xylitol | 15 | 100 | – | — | 100 | 60 | 120 | 120 | 120 | 120 | 150 | 150 |
| Xylitol | 15 | 40 | + | — | 100 | 90 | 120 | 150 | 150 | 150 | 120 | 110 |

Figure 6:
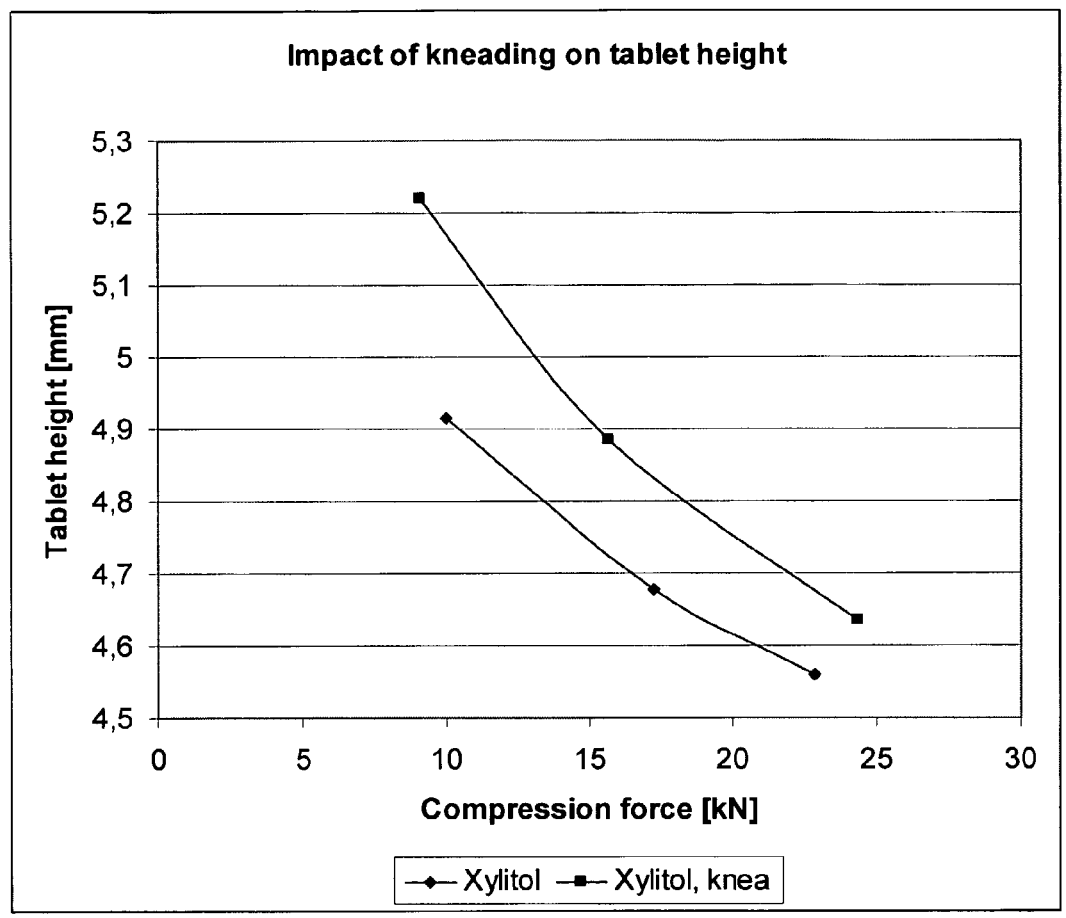
FIG. 6 illustrates the impact of kneading on tablet height based on data from example 3.
Figure 7:
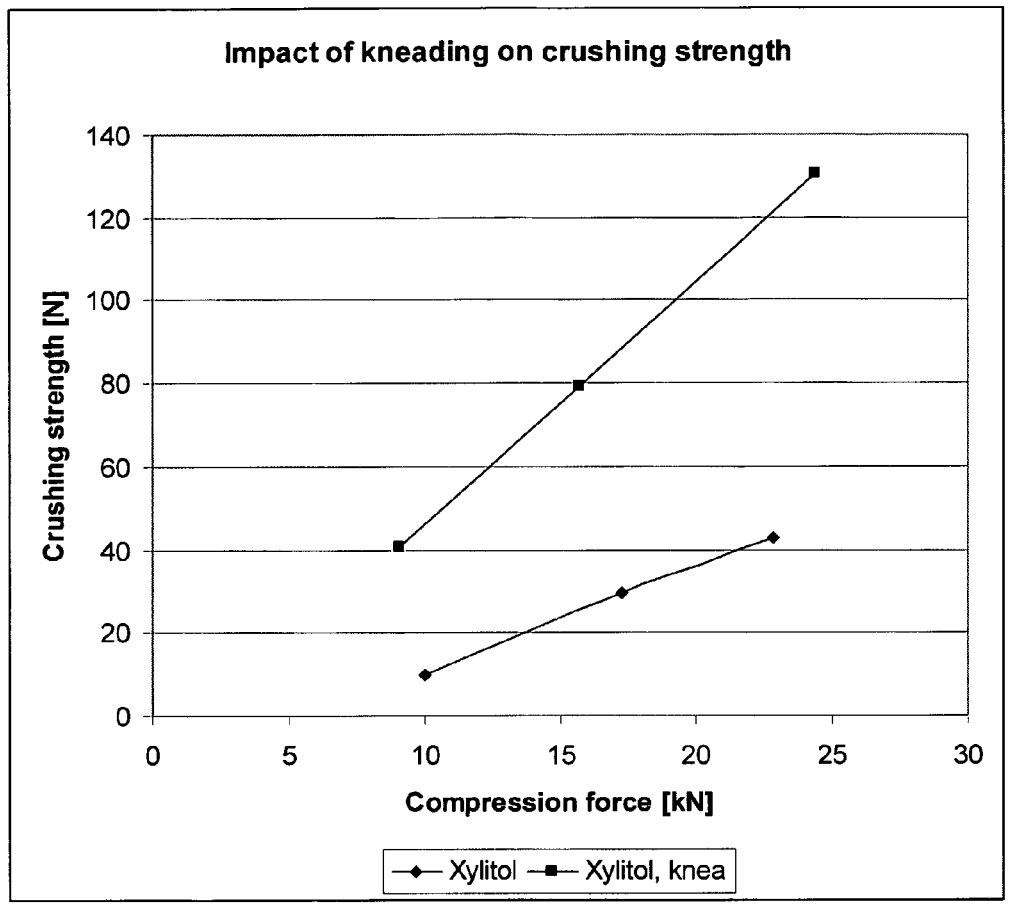
FIG. 7 illustrates the impact of kneading on crushing strength based on data from example 3.

The results are shown in FIGS. 6 and 7.
The analysis of impact of kneading shows that:
Kneading results in tablets with increased crushing strength.
Kneading results in increased tablet height.

The invention claimed is:

1. A method for the preparation of a tablet comprising calcium carbonate as an active substance, the method comprising
   i) melt granulating a composition comprising the calcium carbonate with a sugar alcohol at a temperature that melts or softens the sugar alcohol,
   ii) optionally adding one or more pharmaceutically acceptable excipients, and
   iii) compressing the thus obtained granulate into tablets, wherein the concentration of calcium carbonate in the tablet is at least 60% w/w; and
wherein the tablet has excellent taste and mouth-feel.

2. A method according to claim 1, wherein the melt granulation is performed by extrusion in a screw extruder.

3. A method according to claim 2, wherein the melt granulation is effected by heating at least one segment of the screw extruder to a temperature above the melting point of the sugar alcohol.

4. A method according to claim 3, wherein the temperature is at the most 50° C. above the melting point of the sugar alcohol employed.

5. A method according to claim 1, wherein the sugar alcohol has properties like a binder.

6. A method according to claim 1, wherein the melt granulation is performed using a sugar alcohol selected from the group consisting of isomalt, mannitol, sorbitol, xylitol, inositol, erythritol, lactitol, maltitol, and mixtures thereof.

7. A method according to claim 1, wherein the concentration of the sugar alcohol in the melt granulation step is from about 5% to about 40% w/w based on the total weight of the composition subjected to melt granulation.

8. A method according to claim 1, wherein a further melt binder is included in the composition comprising the calcium-containing compound.

9. A method according to claim 8, wherein a further water-soluble binder is included in the composition comprising the calcium-containing compound.

10. A method according to claim 9, wherein the binder is selected from the group consisting of dextrins, maltodextrins, dextrose, fructose, glucose, inositol, erythritol, isomalt, lactitol, lactose, spray-dried lactose, α-lactose, β-lactose, maltitol, maltose, mannitol, sorbitol, sucrose, tagatose, trehalose, xylitol, low-substituted hydroxypropylcellulose, microcrystalline cellulose, starches or modified starches, potato starch, maize starch, rice starch, pre-gelatinised starch, polyvinylpyrrolidone, polyvinylpyrrolidone/vinyl acetate copolymer, agar, sodium alginate, carboxyalkylcellulose, dextrates, gelatine, gummi arabicum, hydroxypropyl cellulose, hydroxypropylmethylcellulose, methylcellulose, polyethylene glycol, polyethylene oxide, polysaccharides, dextran and soy polysaccharide.

11. A method according to claim 9, wherein the concentration of the binder in the composition comprising calcium carbonate is from about 0.5% to about 40% w/w.

12. A method according to claim 1, wherein the concentration of the sugar alcohol in the composition comprising calcium carbonate is from about 5% to about 40% w/w.

13. A method according to claim 2, wherein the screw extruder is a twin screw extruder.

14. A method according to claim 2, wherein the screw extruder does not have a kneading zone.

15. A method according to claim 2, wherein the screw extruder is equipped with a die plate.

16. A method according to claim 1 further comprising a step of adding one or more therapeutically, prophylactically and/or diagnostically active substance to the granulate obtained.

17. A method according to claim 16, wherein the active substance added is one or more nutrients.

18. A method according to claim 16, wherein the active substance is a D-vitamin.

19. A method according to claim 1, wherein the composition comprising calcium carbonate further comprises sorbitol.

20. A method according to claim 1, wherein the composition comprising calcium carbonate further comprises xylitol.

21. A method according to claim 1, further comprising a step of adding xylitol to the granulate obtained.

22. A method according to claim 1 further comprising a step of adding sorbitol to the granulate obtained.

23. A method according to claim 1, wherein the amount of calcium carbonate in the tablet corresponds to about 100 to about 1000 mg Ca.

24. A method according to claim 1 comprising sorbitol and/or xylitol.

25. A method according to claim 1, wherein the crushing strength of the tablets is adjusted by balancing at least one of:
   i) the concentration of sorbitol contained in the composition comprising the calcium-containing compound,
   ii) the concentration of xylitol contained in the composition comprising the calcium-containing compound,
   iii) the concentration of sorbitol added extragranularly to the granulate
   iv) the concentration of xylitol added extragranularly to the granulate.

26. A granulate obtained as defined in step i) of claim 1, wherein the individual granules at least partly are covered with a sugar alcohol and wherein the concentration of the sugar alcohol in the granulate is from about 5% to about 40% w/w, the concentration of the calcium-containing compound is at least 60% w/w, and the porosity of the granulate is at the most 20%.

27. A pharmaceutical composition comprising a granulate of claim 26.

28. The pharmaceutical composition of claim 27 wherein the composition is in a dosage form.

29. The pharmaceutical composition of claim 27 wherein the composition is in tablet form.

30. The pharmaceutical composition of claim 27 wherein the composition comprises at least 60% w/w of a calcium-containing compound.

31. The pharmaceutical composition of claim 27 wherein the composition is in the form of a chewing tablet.

* * * * *